United States Patent [19]

Wu

[11] 4,251,676

[45] Feb. 17, 1981

[54] SELECTIVE CRACKING REACTIONS BY COFEEDING ORGANIC AMINE OR AMMONIA

[75] Inventor: Margaret M. Wu, Belle Mead, N.J.

[73] Assignee: Mobil Oil Corporation, New York, N.Y.

[21] Appl. No.: 107,807

[22] Filed: Dec. 28, 1979

[51] Int. Cl.$^3$ ................................................. C07C 4/12
[52] U.S. Cl. ....................................................... 585/486
[58] Field of Search ......................................... 585/486

[56] References Cited

U.S. PATENT DOCUMENTS 4,181,811  1/1980  Young ................................. 585/486

Primary Examiner—Curtis R. Davis
Attorney, Agent, or Firm—C. A. Huggett; R. J. Cier

[57] ABSTRACT

An improved process for selective cracking of 1,4-disubstituted aromatic compounds whereby the yield of recyclable olefin cracking product is increased. The process is carried out in the presence of a specified type of crystalline zeolite cracking catalyst (e.g. ZSM-5) and the reactor feed is admixed with ammonia or an organic amine.

11 Claims, No Drawings

SELECTIVE CRACKING REACTIONS BY COFEEDING ORGANIC AMINE OR AMMONIA

BACKGROUND OF THE INVENTION

1. Field of the Invention

This invention is directed to improvements in processes for the selective cracking of dialkylbenzene compounds. It is particularly concerned with increasing the yield of recyclable cracking products of such selective cracking processes.

2. Description of the Prior Art

It has been known and demonstrated that certain shape selective crystalline zeolite catalysts are useful to selectively react the 1,4-isomer of dialkylbenzene compounds in preference to the 1,2- and/or 1,3-isomers. This technology is found to be of significance in the production of 1,3-dialkylbenzenes, since the 1,4-isomer is normally co-produced with the 1,3-isomer and must therefore be removed. Since the boiling points of these isomers are frequently too close together to permit satisfactory fractional distillation on a commercially viable scale, the selective cracking of the undesired 1,4-isomer to the total or near-total exclusion of the 1,3-isomer would be of significant importance.

In such selective cracking reactions it is desirable that the alkyl group be removed intact from the aromatic ring, thereby regenerating the starting olefin and aromatic compounds which in turn may then be recovered and recycled to produce more dialkylbenzene. Unfortunately, what frequently happens is that the alkyl group, once it is removed from the aromatic ring, continues to react on the catalyst to give a spectrum of light hydrocarbons with no recoverable major components.

SUMMARY OF THE INVENTION

It has now been discovered that the selective cracking reaction can be desirably and unexpectedly improved to significantly increase the yield of recyclable olefin in the reaction product. By mixing or cofeeding a minor amount of ammonia or an organic amine with the dialkylbenzene reactant, and then passing the mixture across the shape selective zeolite catalyst, it has been found that one may smoothly convert the 1,4-dialkylbenzene isomer into a smaller aromatic component (e.g. a monoalkylbenzene) and the corresponding olefin. The olefin and aromatic cracking products can then be conveniently and economically recovered for recycle.

The process may be carried out at a temperature of between about 200° C. and 600° C. and a pressure of between about $10^4$ N/m² and $10^6$ N/m². The shape selective zeolite catalysts useful herein are characterized by a silica to alumina ratio of at least about 12 and a constraint index, as hereinafter defined, within the approximate range of 1 to 12.

The amount of ammonia or amine cofed to the catalyst in the dialkylaromatic feed stream, when passed over the selective cracking catalyst, should be between about 0.5 mole % and about 30 mole % relative to the amount of dialkylbenzene therein. It is preferred, however, that the amount of ammonia or amine be between about 1 mole % and 10 mole % of the dialkylbenzene content.

DESCRIPTION OF SPECIFIC EMBODIMENTS

The process of the instant invention is carried out by cofeeding ammonia or an organic amine compound, along with the mixed dialkylbenzene isomers, across a shape selective zeolite catalyst at conditions of temperature and pressure conducive to the selective cracking reaction. As a result thereof, the 1,4-dialkylbenzene isomer is selectively reacted (dealkylated) to give products with significantly lower boiling points than the dialkylbenzene compound, leaving the 1,2- and/or 1,3-dialkylbenzene isomers in excess of their normal equilibrium concentrations. Due to the presence of the ammonia or amine in the feed stream, the initial cracking products pass thru the reactor substantially intact and without further reaction on the catalyst. The reactor effluent can then be processed, using conventional technology, to recover the olefin and aromatic cracking products which in turn may be recycled to an alkylation reactor to make more dialkylbenzene.

The disubstituted aromatic compounds of interest in the process of this invention comprise those defined by the formula:

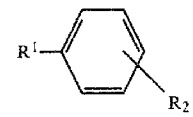

wherein $R^1$ and $R^2$ are alkyl, alkylene or alkyne groups having from one to eight carbon atoms, and $R^1$ is the same as or different from $R^2$. Additionally, it is preferred that at least one of $R^1$ and $R^2$ contain more than one carbon atom. In accordance with this invention, mixtures comprising positional isomers of one or more such compounds, with at least some of the 1,4-isomer present, are brought into contact with the novel type of selective zeolite cracking catalyst. When carried out at suitable conditions of temperature and pressure, the 1,4-isomer will be preferentially dealkylated, in its entirety or at least in substantial part, to yield one or more lower molecular weight aromatic compounds and an olefin corresponding to the alkyl group which was removed therefrom.

By cofeeding from about 0.5 mole % to about 30 mole %, and preferably from 1 mole % to 10 mole % (measured relative to the dialkylbenzene concentration) of ammonia or an organic amine along with the dialkylbenzene reactant, one may prevent further reaction of the initial olefin product on the catalyst. Suitable organic amines include, but are not limited to: aniline; N-substituted anilines (e.g. N-methyl aniline, N,N-dimethylaniline, diphenylamine); ring-substituted anilines (e.g. chloroanilines, toluidines); N-methylamine; N,N-dimethylamine; pyridine; picolines; and others.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred in some applications to use zeolites having higher silica/alumina ratios of at least about 30. In addition, zeolites as otherwise characterized herein but which are substantially free of aluminum, i.e. having silica to alumina mole ratios of 1,600 and higher, are found to be useful and even preferable in some instances. Such "high silica" zeolites are intended to be included within this description. The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\frac{\log 10 \text{ (fraction of hexane remaining)}}{\log 10 \text{ (fraction of 3-methylpentane remaining)}}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, and other similar materials.

ZSM-5 is described in greater detail in U.S. Pat. Nos. 3,702,886 and 3,941,871. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed catalyst, is incorporated herein by reference.

ZSM-35 is described in U.S. Pat. No. 4,016,245. The description of that catalyst, and particularly the X-ray diffraction pattern thereof, is incorporated herein by reference.

ZSM-38 is more particularly described in U.S. Pat. No. 4,046,859. The description of that catalyst, and particularly the specified X-ray diffraction pattern thereof, is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint," which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35 and ZSM-38, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures.

This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The process of this invention may be carried out as a batch-type, semi-continuous or continuous operation utilizing a fixed, fluidized or moving bed catalyst system. The catalyst after use in a moving bed reactor is conducted to a regeneration zone wherein coke is burned from the catalyst in an oxygen-containing atmosphere, e.g. air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5–2%) is used to burn the coke in a controlled manner so as to limit the temperature to a maximum of around 500°–550° C.

The process may be carried out in a system wherein the disubstituted compounds are in either the liquid or the vapor state, and the mixture of disubstituted aromatic compounds may be substantially pure (i.e. contain no substantial quantity of hydrocarbon material other than one or more isomers of said disubstituted aromatic material) or may contain amounts of other hydrocarbon material. The latter situation is such as would exist, for example, when the feed stream for the instant process also comprises the effluent stream of an earlier upstream process, such as a process for the manufacture of disubstituted aromatic compounds. Also, the feed stream for the process of this invention may contain other inert materials as diluents or solvents. Suitable diluents include, but are not limited to: methane, nitrogen, propane, hexane, steam, carbon dioxide, helium, and so forth.

The feed stream, including the minor amount of ammonia or organic amine, is brought into contact with the zeolite catalyst at temperatures of between about 200° C. and 600° C., a pressure of between about $10^4 N/m^2$ and about $10^6 N/m^2$ (0.1–10 atmospheres), and a feed weight hourly space velocity (WHSV) of between about 0.5 and about 20. The latter WHSV is based upon the weight of the catalyst compositions, i.e. the total weight of active catalyst and binder therefor. It is preferred that contact between the catalyst and the reactants be carried out at from about 300° C. to about 450° C. with a feed WHSV of between 1 and 10. Although the reaction normally takes place at atmospheric pressure (i.e. $10^5 N/m^2$), the preferred pressure range extends from about $5 \times 10^4 N/m^2$ to about $2 \times 10^5 N/m^2$.

The 1,2- and/or 1,3-dialkylbenzene compounds may be separated from the reactor product stream by any suitable means, such as, for example, conventional distillation. The olefinic cracking product, which will substantially comprise the intact alkyl group which had been removed from the dealkylated aromatic compound, may likewise be recovered by conventional means, as may the aromatic portion of the cracking product. In an especially preferred embodiment, the reactor effluent stream is continuously distilled for separate but simultaneous recovery of the desired dialkylbenzene isomers, the olefinic cracking product, and the lower MW aromatic cracking product. The recovered olefinic and aromatic cracking products are then recycled to an alkylation reaction system to be recombined to produce more dialkylbenzene, which in turn is selectively cracked in the instant process to remove the 1,4-dialkylbenzene isomer, and so on, thereby maximizing the utilization of all of the materials involved and significantly reducing wasteful and uneconomic by-products.

Understanding of the disclosed invention will be facilitated by consideration of the following illustrative examples, which should not be taken as limiting on the scope of the concept embodied herein.

EXAMPLE 1

A sample of $NH_4ZSM-5$ (65 wt %ZSM-5, 35 wt % alumina binder; ZSM-5 silica/alumina mole ratio=70) was calcined in air at 500° C. to convert the ammonium form into the hydrogen form. Four grams of the calcined catalyst were placed in a quartz reactor and heated to 400° C. A feed stream, comprising 5.0% 1-isopropyl-2-methylbenzene, 67.8% 1-isopropyl-3-methylbenzene and 27.4% 1-isopropyl-4-methylbenzene, was passed through the reactor at WHSV of 1.2. The liquid and gaseous products were collected separately and analyzed via gas chromatography. The product compositions are shown in Table I. As will be seen, the catalyst was very selective for removing the 1,4-isomer from the mixture, the 1-isopropyl-4-methylbenzene having been reduced by 95.4% versus 11.1% reduction of the 1,3-isomer. However, the non-aromatic cracking products contained only 15.3 mole % of propylene, the major portion of the non-aromatic product having been converted to other hydrocarbons which would be difficult to separate, hence making it impractical to recycle the gaseous product of the reaction.

TABLE I

Catalyst: HZSM-5
Temperature: 400° C.
Feed WHSV: 1.2

| Composition, mole % | Starting Material | Products |
|---|---|---|
| (LIQUIDS) | | |
| Toluene | 0 | 24.2 |
| $C_8$—$C_9$ aromatic | 0 | 6.8 |
| Isopropylmethylbenzenes: | | |
| 1,2-isomer | 5.0 | 5.4 |
| 1,3-isomer | 67.8 | 60.3 |
| 1,4-isomer | 27.4 | 0.9 |
| n-Propylmethylbenzene | 0 | 2.4 |
| Total | 100.2 | 100.0 |
| (GASEOUS) | | |
| $CH_4$ | — | 0 |
| $C_2H_6 + CO_2$ | — | 3.3 |
| $C_2H_4$ | — | 0.1 |
| $C_3H_8$ | — | 34.3 |
| $C_3H_6$ | — | 15.3 |
| i-$C_4H_{10}$ | — | 33.2 |
| n-$C_4H_{10}$ | — | 8.6 |
| Others | — | 5.2 |
| Total | | 100.0 |

% Conversion of isopropylbenzenes

| 1,2-isomer | (−9.2%) |
|---|---|
| 1,3-isomer | 11.1% |
| 1,4-isomer | 95.4% |

EXAMPLE 2

Using the same ZSM-5 catalyst and isopropylmethylbenzene feed as in Example 1, three runs were conducted with different amounts of aniline (aminobenzene) mixed with the feed stream. The liquid and gaseous products were collected and analyzed as in Example 1. The results are shown in Tables II through IV.

TABLE II

Catalyst: HZSM-5
Temperature: 400° C.
Feed WHSV: 1.4

| Composition, mole % | Starting Material | Products |
|---|---|---|
| (LIQUIDS) | | |
| Toluene | 0 | 20.9 |
| Isopropylmethylbenzenes: | | |
| 1,2-isomer | 4.6 | 4.0 |
| 1,3-isomer | 64.6 | 63.0 |
| 1,4-isomer | 25.0 | 5.1 |
| n-Propylmethylbenzene | 0 | 1.1 |
| Aniline | 8.2 | 6.0 |
| Others | 0.6 | 0.1 |
| Total | 100.0 | 100.2 |
| (GASEOUS) | | |
| CO | — | 0.4 |
| $CH_4$ | — | 0.4 |
| $C_2H_6 + CO_2$ | — | 0.8 |
| $C_2H_4$ | — | 0.9 |
| $C_3H_8$ | — | 1.4 |
| $C_3H_6$ | — | 93.7 |
| $C_4H_{10}$ | — | 0.9 |
| Others | — | 1.6 |
| Total | | 100.0 |

% Conversion of isopropylbenzenes

| 1,2-isomer | 21.9% |
|---|---|
| 1,3-isomer | (−2.2%) |
| 1,4-isomer | 79.7% |

TABLE III

Catalyst: HZSM-5
Temperature: 400° C.
Feed WHSV: 1.4

| Composition, mole % | Starting Material | Products |
|---|---|---|
| (LIQUIDS) | | |
| Toluene | 0 | 26.6 |
| Isopropylmethylbenzenes: | | |
| 1,2-isomer | 4.7 | 4.4 |
| 1,3-isomer | 63.9 | 62.0 |
| 1,4-isomer | 25.9 | 2.4 |
| n-Propylmethylbenzene | 0 | 0.9 |
| Aniline | 5.4 | 3.4 |
| Others | 0.1 | 0.5 |
| Total | 100.0 | 100.2 |
| (GASEOUS) | | |
| CO | — | 0.2 |
| $CH_4$ | — | 0.3 |
| $C_2H_6 + CO_2$ | — | 0.5 |
| $C_2H_4$ | — | 0.7 |
| $C_3H_8$ | — | 1.5 |
| $C_3H_6$ | — | 94.1 |
| $C_4H_{10}$ | — | 1.4 |
| Others | — | 1.2 |
| Total | — | 99.9 |

% Conversion of isopropylbenzenes

| 1,2-isomer | 7.5% |
|---|---|
| 1,3-isomer | 2.1% |
| 1,4-isomer | 90.7% |

TABLE Iv

Catalyst: HZSM-5
Temperature: 420° C.
Feed WHSV: 1.4

TABLE IV-continued

| Composition, mole % | Starting Material | Products |
|---|---|---|
| (LIQUIDS) | | |
| Toluene | 0 | 2.2 |
| Isopropylmethylbenzenes: | | |
| 1,2-isomer | 4.8 | 4.3 |
| 1,3-isomer | 67.4 | 59.2 |
| 1,4-isomer | 24.4 | 1.1 |
| n-Propylmethylbenzene | 0 | 0 |
| Aniline | 3.3 | 2.8 |
| Others | 0 | 0.3 |
| Total | 99.9 | 99.9 |
| (GASEOUS) | | |
| CO | — | 0.9 |
| CH$_4$ | — | 0.8 |
| C$_2$H$_6$ + CO$_2$ | — | 0.7 |
| C$_2$H$_4$ | — | 2.6 |
| C$_3$H$_8$ | — | 4.0 |
| C$_3$H$_6$ | — | 82.3 |
| C$_4$H$_{10}$ | — | 0.4 |
| Others | — | 8.4 |
| Total | | 100.1 |

| Conversion of isopropylbenzenes | |
|---|---|
| 1,2-isomer | 10.3% |
| 1,3-isomer | 12.1% |
| 1,4-isomer | 95.3% |

In each run the 1-isopropyl-4-methylbenzene was selectively cracked relative to the 1,2- and 1,3-isomers. As will be seen, the addition of the amine has prevented the destruction of the primary non-aromatic cracking product, i.e. propylene. At 8.8% aniline in the feed stream, the gaseous product contained 93.7 mole % propylene; at 5.4% aniline level the gaseous product was 94.1 mole % propylene; and at 3.3% aniline it was 82.3 mole % propylene.

EXAMPLE 3

Again using the ZSM-5 catalyst and isomeric mixture of isopropylmethylbenzenes of Example 1, ammonia was cofed to the catalyst at 350° C. in two runs at 0.5 wt % and 2.0 wt %, respectively. The feed WHSV was 1.4. The products were collected and analyzed as before and the results are summarized in Tables V and VI.

TABLE V

Catalyst: HZSM-5
Temperature: 350° C.
Feed WHSV: 1.4

| Composition, mole % | Starting Material | Products |
|---|---|---|
| (LIQUIDS)* | | |
| Toluene | 0 | 14.8 |
| Isopropylmethylbenzenes: | | |
| 1,2-isomer | 5.0 | 4.9 |
| 1,3-isomer | 67.1 | 54.5 |
| 1,4-isomer | 27.2 | 3.1 |
| n-Propylmethylbenzene | 0 | 0.6 |
| Others | 0.7 | 2.2 |
| Total | 100.0 | 100.1 |
| (GASEOUS) | | |
| CO | — | 0 |
| CH$_4$ | — | 0.1 |
| C$_2$H$_6$ + CO$_2$ | — | 0.4 |
| C$_2$H$_4$ | — | 15.0 |
| C$_3$H$_8$ | — | 3.8 |
| C$_3$H$_6$ | — | 46.7 |
| C$_4$H$_{10}$ | — | 1.5 |
| C$_4$H$_8$ | — | 7.7 |
| Others | — | 2.8 |
| Total | | 100.0 |

| % Conversion of isopropylbenzenes | |
|---|---|
| 1,2-isomer | 1.6% |
| 1,3-isomer | 19.4% |
| 1,4-isomer | 88.4% |

*Calculation of the liquid product includes only aromatic components. The low-boiling non-aromatic components comprised mostly ammonia and some amines.

TABLE VI

Catalyst: HZSM-5
Temperature: 350° C.
Feed WHSV: 1.4

| Composition, mole % | Starting Material | Products |
|---|---|---|
| (LIQUIDS)* | | |
| Toluene | 0 | 12.2 |
| Isopropylmethylbenzenes: | | |
| 1,2-isomer | 5.0 | 4.3 |
| 1,3-isomer | 67.1 | 64.7 |
| 1,4-isomer | 27.2 | 18.8 |
| Others | 0.7 | 0 |
| Total | 100.0 | 100.0 |
| (GASEOUS) | | |
| CO | — | 0.5 |
| CH$_4$ | — | 0.4 |
| CH$_2$H$_6$ + CO$_2$ | — | 0.5 |
| C$_2$H$_4$ | — | 3.4 |
| C$_3$H$_8$ | — | 4.8 |
| C$_3$H$_6$ | — | 68.5 |
| C$_4$H$_{10}$ | — | 6.8 |
| C$_4$H$_8$ | — | 12.8 |
| Others | — | 2.4 |
| Total | | 100.0 |

| Conversion of isopropylbenzenes | |
|---|---|
| 1,2-isomer | 14.1% |
| 1,3-isomer | 4.3% |
| 1,4-isomer | 31.4% |

*Calculation of the liquid product includes only aromatic components. The low-boiling non-aromatic components comprised mostly ammonia and some amines.

The major non-aromatic cracking product was again propylene. At the 0.5 wt % level of ammonia in the feed stream, the gaseous cracking product contained 46.7 mole % propylene. When the level of ammonia was increased to 2.0 wt % of the feed stream, the amount of propylene in the non-aromatic product increased to 68.5 mole %.

Having thus generally described the process of the present invention and set forth specific examples in support thereof, it is to be understood that no undue restrictions are to be imposed on the scope of the concept disclosed and claimed herein by reason of the illustrative examples.

I claim:

1. In the process for selective cracking of 1,4-disubstituted aromatic compounds in the presence of crystalline zeolite catalysts, said zeolites being characterized by a constraint index within the approximate range of 1 to 12 and a silica to alumina mole ratio of at least 12, the improvement comprising: contacting said disubstituted aromatic compounds with said zeolite in the presence of ammonia or an organic amine.

2. The improved process of claim 1 wherein said ammonia or organic amine is mixed with said disubstituted aromatic compounds prior to contacting said compounds with said zeolite.

3. The process of claim 1 wherein said ammonia or organic amine is present in an amount of between about 0.5 mole percent and about 30 mole percent of the disubstituted aromatic compound concentration.

4. The process of claim 3 wherein said ammonia or organic amine is present in an amount of between 1 mole percent and 10 mole percent of the disubstituted aromatic compound concentration.

5. The process of claim 1 wherein said disubstituted aromatic compounds comprise compounds defined by the formula:

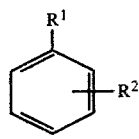

wherein $R^1$ and $R^2$ are alkyl, alkylene or alkyne groups having from one to eight carbon atoms and $R^1$ is the same as or different than $R^2$ and, further, wherein at least one of $R^1$ and $R^2$ contains more than one carbon atom.

6. The process of claim 1 wherein said contacting is carried out at a temperature of between about 200° C. and about 600° C. and a pressure of from $10^4$ N/m$^2$ to $10^6$ N/m$^2$.

7. The process of claim 6 wherein said temperature is between about 300° C. and about 450° C.

8. The process of claim 7 wherein said pressure is between $5 \times 10^4$ N/m$^2$ and $2 \times 10^5$ N/m$^2$.

9. The process of claim 1 wherein said crystalline zeolite is chosen from the group consisting of: ZSM-5; ZSM-11; ZSM-12; ZSM-23; ZSM-35 and ZSM-38.

10. The process of claim 1 wherein said crystalline zeolite is ZSM-5.

11. The process of claim 1, 9 or 10 wherein said zeolite additionally comprises a binder therefor.

* * * * *